(12) United States Patent
Constantz et al.

(10) Patent No.: US 8,771,748 B2
(45) Date of Patent: *Jul. 8, 2014

(54) RAPID SETTING CALCIUM PHOSPHATE CEMENTS

(75) Inventors: Brent R. Constantz, Cupertino, CA (US); David Delaney, Scotts Valley, CA (US); Duran Yetkinler, Cupertino, CA (US)

(73) Assignee: Skeletal Kinetics, LLC, Cupertino, CA (US)

( * ) Notice: Subject to any disclaimer, the term of this patent is extended or adjusted under 35 U.S.C. 154(b) by 868 days.

This patent is subject to a terminal disclaimer.

(21) Appl. No.: 11/134,051

(22) Filed: May 19, 2005

(65) Prior Publication Data

US 2005/0260279 A1  Nov. 24, 2005

Related U.S. Application Data

(63) Continuation-in-part of application No. 10/850,985, filed on May 20, 2004, now Pat. No. 7,252,841.

(51) Int. Cl.
| | | |
|---|---|---|
| A61K 9/14 | (2006.01) | |
| A61K 33/42 | (2006.01) | |
| A61K 33/06 | (2006.01) | |
| A61F 2/28 | (2006.01) | |
| C04B 12/02 | (2006.01) | |
| C04B 7/00 | (2006.01) | |

(52) U.S. Cl.
USPC ........... 424/602; 424/423; 424/489; 424/724; 623/23.62; 623/16.11; 623/23.61; 106/638; 106/690

(58) Field of Classification Search
None
See application file for complete search history.

(56) References Cited

U.S. PATENT DOCUMENTS

| | | | |
|---|---|---|---|
| 4,160,012 A | 7/1979 | Ono et al. | |
| 4,161,511 A | 7/1979 | Shiraki et al. | |
| 4,429,691 A | 2/1984 | Niwa et al. | |
| 4,497,075 A | 2/1985 | Niwa et al. | |
| 4,990,163 A | 2/1991 | Ducheyne et al. | |
| 5,013,323 A | 5/1991 | Kobayashi et al. | |
| 5,092,888 A | 3/1992 | Iwamoto et al. | |
| 5,281,265 A | 1/1994 | Liu | |
| 5,525,148 A | 6/1996 | Chow et al. | |
| 5,545,254 A | 8/1996 | Chow et al. | |
| 5,580,623 A | 12/1996 | Fulmer et al. | |
| 5,679,294 A | 10/1997 | Umezu et al. | |
| 5,695,729 A | 12/1997 | Chow et al. | |
| 5,697,981 A | 12/1997 | Ison et al. | |
| 5,900,254 A | 5/1999 | Constantz | |
| 5,954,867 A | 9/1999 | Chow et al. | |
| 5,962,028 A | 10/1999 | Constantz | |
| 5,968,253 A | 10/1999 | Poser et al. | |
| 5,976,234 A | 11/1999 | Chow et al. | |
| 5,997,624 A | 12/1999 | Chow et al. | |
| 6,005,162 A | 12/1999 | Constantz | |
| 6,027,742 A | 2/2000 | Lee et al. | |
| 6,139,578 A | 10/2000 | Lee et al. | |
| 6,375,935 B1 | 4/2002 | Constantz | |
| 6,379,453 B1 | 4/2002 | Lin et al. | |
| 6,537,360 B2 * | 3/2003 | Miyama et al. ............... 106/35 |
| 6,840,995 B2 | 1/2005 | Lin et al. | |
| 2002/0155167 A1 | 10/2002 | Lee et al. | |
| 2003/0199615 A1 | 10/2003 | Chaput et al. | |
| 2004/0076685 A1 | 4/2004 | Tas | |

FOREIGN PATENT DOCUMENTS

| | | | |
|---|---|---|---|
| CA | 2383580 A1 | 2/2002 | |
| DE | 4016135 A1 | 11/1990 | |
| JP | 5168692 | 7/1993 | |
| JP | 10017349 A | 1/1998 | |
| JP | 10504467 A | 5/1998 | |
| JP | 2001106638 A | 4/2001 | |
| JP | 2003531798 A | 10/2003 | |
| JP | 2004502626 A | 1/2004 | |
| WO | 0202478 | 1/2002 | |
| WO | WO-02056929 * | 7/2002 | |
| WO | WO 02/062721 A1 * | 8/2002 | ............. C04B 12/02 |

OTHER PUBLICATIONS

Bohner et al. "Technological Issues for the Development of More Efficient Calcium Phosphate Bone Cements: A Critical Assessment," (2005) Biomaterials, 26:6423-6429.

* cited by examiner

*Primary Examiner* — Ernst Arnold
*Assistant Examiner* — Jianfeng Song
(74) *Attorney, Agent, or Firm* — Bozicevic, Field & Francis LLP; Bret E. Field; Benjamin C. Pelletier

(57) ABSTRACT

Methods are provided for producing compositions, e.g. pastes or clays, which rapidly set into high-strength calcium phosphate products. In the subject methods, dry reactants that include calcium and phosphate sources, as well as a monovalent cation dihydrogen phosphate salt, are combined with a setting fluid and the combined reactants are mixed to produce the settable composition. A feature of the invention is that cements rapidly set into high strength product compositions. Also provided are the compositions themselves as well as kits for preparing the same. The subject methods and compositions produced thereby find use in a variety of applications, including hard tissue repair applications.

27 Claims, No Drawings

RAPID SETTING CALCIUM PHOSPHATE CEMENTS

CROSS-REFERENCE TO RELATED APPLICATIONS

This application is a continuation-in-part of application Ser. No. 10/850,985, now U.S. Pat. No. 7,252,841, filed on May 20, 2004; the disclosure of which is herein incorporated by reference.

BACKGROUND

Calcium phosphate cements that are prepared by combining a dry component(s) and a liquid to form a flowable paste-like material that is subsequently capable of setting into a solid calcium phosphate product hold great promise for use as structural materials in the orthopedic and dental fields. For example, it is desirable to be able to inject a flowable material into a cancellous bone void and have the material set into a solid calcium phosphate mineral product that is capable of withstanding physiological loads. Materials that set into solid calcium phosphate mineral products are of particular interest as such products can closely resemble the mineral phase of natural bone and are susceptible to remodeling, making such products extremely attractive for use in orthopedics and related fields.

While a large number of different calcium phosphate cement formulations have been developed, there is a continued need for the development of yet more advanced formulations. Of particular interest is the development of formulations that rapidly set into strong materials. The present invention provides such formulations.

RELEVANT LITERATURE

U.S. patents of interest include: U.S. Pat. Nos. 6,375,935; 6,139,578; 6,027,742; 6,005,162; 5,997,624; 5,976,234; 5,968,253; 5,962,028; 5,954,867; 5,900,254; 5,697,981; 5,695,729; 5,679,294; 5,580,623; 5,545,254; 5,525,148; 5,281,265; 5,092,888; 5,013,323, 4,990,163; 4,497,075; 4,429,691; 4,161,511 and 4,160,012.

SUMMARY OF THE INVENTION

Methods are provided for producing compositions, e.g. pastes or clays, which rapidly set into high-strength calcium phosphate products. In the subject methods, dry reactants that include calcium and phosphate sources, as well as a monovalent cation dihydrogen phosphate salt, are combined with a setting fluid and the combined reactants are mixed to produce the settable composition. A feature of the invention is that cements rapidly set into high strength product compositions. Also provided are the compositions themselves as well as kits for preparing the same. The subject methods and compositions produced thereby find use in a variety of applications, including hard tissue repair applications.

DESCRIPTION OF THE SPECIFIC EMBODIMENTS

Methods are provided for producing compositions, e.g. pastes or clays, which rapidly set into high-strength calcium phosphate products. In the subject methods, dry reactants that include calcium and phosphate sources, as well as a monovalent cation dihydrogen phosphate salt, are combined with a setting fluid and the combined reactants are mixed to produce the settable composition. A feature of the invention is that cements rapidly set into high strength product compositions. Also provided are the compositions themselves as well as kits for preparing the same. The subject methods and compositions produced thereby find use in a variety of applications, including hard tissue repair applications.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In further describing the subject invention, the subject methods will be described first, followed by a description of the compositions produced thereby, kits for use in preparing the same and methods for using the subject compositions in methods of hard tissue, e.g. bone repair.

Methods

In the subject methods, dry reactants that include a calcium source and a phosphate source, as well as a sodium dihydrogen phosphate salt, are combined with a setting fluid under conditions sufficient to produce a settable, e.g., flowable, composition that rapidly sets into a high-strength calcium-phosphate containing product, even when immersed in a fluid environment.

In the subject methods, the dry reactants include a calcium source and a phosphate source. The dry reactants are typically particulate compositions, e.g., powders, where the particle size of the components of the particulate compositions typically ranges from about 1 to about 1000 microns, usually from about 1 to about 500 microns and more usually from about 1 to about 200 microns.

As mentioned above, the dry reactants include a calcium source and a phosphate source. The calcium source and phosphate source may be present as a single compound or present as two or more compounds. As such, a single calcium phosphate present in the dry reactants may be the calcium source and the phosphate source. Alternatively, two or more compounds may be present in the dry reactants, where the compounds may be compounds that include calcium, phosphate or calcium and phosphate. Calcium phosphate sources of interest that may be present in the dry reactants include: DCPD (dicalcium phosphate dihydrate, brushite or $CaHPO_4.2H_2O$), ACP (amorphous calcium phosphate or $Ca_3(PO_4)_2.H_2O$), DCP (dicalcium phosphate, monetite or $CaHPO_4$), tricalcium phosphate, including both α- and β-$(Ca_3(PO_4)_2)$, tetracalcium phosphate $(Ca_4(PO_4)_2O)$, etc. Calcium sources of interest include, but are not limited to: calcium carbonate $(CaCO_3)$, calcium oxide (CaO), calcium hydroxide $(Ca(OH)_2)$ and the like. Phosphate sources of interest include, but are not limited to: phosphoric acid $(H_3PO_4)$, soluble phosphates, and the like.

In certain embodiments, the dry reactant portion or component of the cement includes a calcium and/or phosphate dry reactant that has a mean particle size (as determined using the Horiba LA-300 laser diffraction particle sizer (Version 3.30 software for Windows 95) (Irvine, Calif.)) of less than about 8 μm and a narrow particle size distribution, as described in copending U.S. patent application Ser. No. 10/900,029, now U.S. Pat. No. 7,175,858, the disclosure of which is herein incorporated by reference. As such, the dry reactant component of the cement, which may include one or more distinct dry reactants, includes a reactant that has a mean particle size of less than about 8 μm and a narrow particle size distribution. The mean particle size of this reactant may vary, ranging in representative embodiments from about 1 to about 7 μm, such as from about 1 to about 6 μm, including from about 1 to about 5 μm, where the mean particle size in certain embodiments may be about 1, about 2, about 3 and about 4 μm, where in certain embodiments the mean particle size is about 3 μm.

This particular reactant of the subject cement compositions is further characterized in that it has a narrow particle size distribution. By narrow particle size distribution is meant that the standard deviation of the particles that make up the particular reactant population (as determined using the Horiba LA-300 laser diffraction particle sizer (Version 3.30 software for Windows 95) (Irvine, Calif.)) does not exceed about 4.0, and in certain representative embodiments does not exceed about 3.0, e.g., does not exceed about 2.5, including does not exceed about 2.0 μm.

This particular reactant of the subject cement compositions is further characterized in that mode (as determined using the Horiba LA-300 laser diffraction particle sizer (Version 3.30 software for Windows 95) (Irvine, Calif.)) does not exceed about 8.0, and in certain representative embodiments does not exceed about 6.0, e.g., does not exceed about 5, including does not exceed about 3.0 μm.

In certain embodiments, the above described first reactant makes up the entire dry reactants of the composition, such that it makes up 100% of the dry component of the composition.

In certain embodiments, the dry reactants are further characterized by including a second reactant that has mean particle size that is at least 2 times larger than the mean particle size of the first reactant component, where the mean particle size of this second reactant may be at least about 9 μm, at least about 10 μm, at least about 20 μm, at least about 25 μm, at least about 30 μm or larger (as determined using the Horiba LA-300 laser diffraction particle sizer (Version 3.30 software for Windows 95) (Irvine, Calif.)).

In certain embodiments, the amount of the first reactant component of the dry reactant composition is greater than the total amount of other reactant components that may be present, such as the second reactant component as described above. In these embodiments, the mass ratio of the first reactant component to the total mass of the dry reactants may range from about 1 to about 10, e.g., from about 9 to about 6, such as from about 9 to about 7, including from about 9.5 to about 8.5.

In certain representative embodiments, the first reactant component is a calcium phosphate compound having a calcium to phosphate ratio ranging from about 1.0 to about 2.0, including from about 1.33 to about 1.67, such as 1.5. In certain embodiments, the calcium phosphate compound is a tricalcium phosphate, such as α- and β-tricalcium phosphate, where in certain representative embodiments, the tricalcium phosphate is α-tricalcium phosphate.

As indicated above, a feature of the subject invention is that the dry reactants further include a monovalent cation dihydrogen phosphate salt. By monovalent cation dihydrogen phosphate salt is meant a salt of a dihydrogen phosphate anion and a monovalent cation, e.g., K+, Na+, etc., where the salt may or may not include one or more water molecules of hydration, e.g., may be anhydrous, a monohydrate, a dihydrate, etc. The monovalent cation dihydrogen phosphate salts present in the cements of the subject invention may be described by the following formula:

$$Y^+H_2PO_4.(H_2O)_n$$

where:

$Y^+$ is a monovalent cation, such as K+, Na+, etc.; and n is an integer from 0 to 2.

In certain representative embodiments, the salt is a sodium dihydrogen phosphate salt, such as sodium biphosphate (i.e., sodium phosphate monobasic, $NaH_2PO_4$), or the monohydrate $(NaH_2PO_4.H_2O)$ or dihydrate $(NaH_2PO_4.2H_2O)$ thereof.

The amount of monovalent cation dihydrogen phosphate salt that is present in the dry reactants may vary, but is typically present in an amount sufficient to provide for a rapidly setting high strength attainment composition, as described in greater detail below. In representative embodiments, the salt is present in an amount that ranges from about 0.10 to about 10 wt. %, such as from about 0.2 to about 5.0 wt %, including from about 0.5 to about 2.0 wt. % of the total weight of the dry reactants.

A variety of calcium phosphate cement compositions are known to those of skill in the art, and such cements may be readily modified into cements of the subject invention by including a water-soluble contrast agent, as described below. Cement compositions known to those of skill in the art and of interest include, but are not limited to, those described in U.S. Pat. Nos. 6,027,742; 6,005,162; 5,997,624; 5,976,234; 5,968,253; 5,962,028; 5,954,867; 5,900,254; 5,697,981; 5,695,729; 5,679,294; 5,580,623; 5,545,254; 5,525,148; 5,281,265; 4,990,163; 4,497,075; and 4,429,691; the disclosures of which are herein incorporated by reference.

The ratios or relative amounts of each of the disparate calcium and/or phosphate compounds in the dry reactant mixture is one that provides for the desired calcium phosphate product upon combination with the setting fluid and subsequent setting. In many embodiments, the overall ratio (i.e., of all of the disparate calcium and/or phosphate compounds in the dry reactants) of calcium to phosphate in the dry reactants ranges from about 4:1 to 0.5:1, usually from about 2:1 to 1:1 and more usually from about 1.9:1 to 1.33:1.

The second component of the subject cement compositions is a setting fluid, as summarized above. The setting fluid can be any of a variety of setting fluids known to those of skill in the art. Setting fluids include a variety of physiologically compatible fluids, including, but are not limited to: water (including purified forms thereof), aqueous alkanol solutions, e.g. glycerol, where the alkanol is present in minor amounts, preferably less than about 20 volume percent; pH buffered or non-buffered solutions; solutions of an alkali metal hydroxide, acetate, phosphate or carbonate, particularly sodium, more particularly sodium phosphate or carbonate, e.g., at a concentration in the range of about 0.01 to about 2M, such as from about 0.05 to about 0.5M, and at a pH in the range of about 6 to about 11, such as from about 7 to about 9, including from about 7 to about 7.5; and the like.

Of particular interest in certain embodiments is a silicate setting fluid, i.e., a setting fluid that is a solution of a soluble silicate. By solution of a soluble silicate is meant an aqueous solution in which a silicate compound is dissolved and/or suspended. The silicate compound may be any compound that is physiologically compatible and is soluble in water. By soluble in water is meant a concentration of at least about 1%, usually at least about 2% and more usually at least about 5%, where the concentration of the silicate employed typically ranges from about 0-0.1 to 20%, usually from about 0.01-5 to 15% and more usually from about 5 to 10%.

Representative silicates of interest include, but are not limited to: sodium silicates, potassium silicates, borosilicates, magnesium silicates, aluminum silicates, zirconium silicates, potassium aluminum silicates, magnesium aluminum silicates, sodium aluminum silicates, sodium methylsilicates, potassium methylsilicates, sodium butylsilicates, sodium propylsilicates, lithium propylsilicates, triethanol ammonium silicates, tetramethanolamine silicates, zinc hexafluorosilicate, ammonium hexafluorosilicate, cobalt hexafluorosilicate, iron hexafluorosilicate, potassium hexafluorosilicate, nickel hexafluorosilicate, barium hexafluorosilicate, hydroxyammonium hexafluorosilicate, sodium hexafluorosilicate and calcium fluorosilicate. The preparation of sodium hexafluorosilicate is described in U.S. Pat. Nos. 4,161,511 and 4,160,012; the disclosures of which are herein incorporated by reference. Of particular interest in many embodiments are solutions of sodium silicate, where the manufacture of dry sodium silicate ($Na_2SiO_3$, $Na_6Si_2O_7$ and $Na_2Si_3O_7$) is described in Faith, Keyes & Clark's INDUSTRIAL CHEMICALS (1975) pp 755-761.

In certain embodiments, the solution may further include an amount of phosphate ion, as described in U.S. application Ser. No. 10/462,075; the disclosure of which is herein incorporated by reference.

In certain embodiments, an emulsifying agent is included in the formulation. Emulsifying agents of interest include, but are not limited to: polyoxyethylene or polyoxypropylene polymers or copolymers thereof, such as polyethylene glycol and polypropylene glycol; nonionic cellulose ethers such as methylcellulose, ethylcellulose, hydroxymethylcellulose, hydroxyethylcellulose, carboxymethylcellulose, carboxyethylcellulose and hydroxypropylcellulose; additional celluloses, such as carboxymethylcellulose sodium, carboxymethylcellulose calcium, carboxymethylstarch; polysaccharides produced by microbial fermentation, such as yeast glucans, xanthan gum, b-1,3-glucans (which may be straight-chained or branched; e.g. curdlan, paramylum, pachyman, scleroglucan, laminaran); other natural polymers, e.g., gum arabic, guar gum, carrageenin, gum tragacanth, pectin, starch, gelatin, casein, dextrin, cellulose; polyacrylamide; polyvinyl alcohol; starch; starch phosphate; sodium alginate and propylene glycol alginate; gelatin; amino-containing acrylic acid copolymers and quaternization products derived therefrom; and the like.

In certain embodiments of particular interest, the emulsifying agent is a cellulose ether, particularly a nonionic cellulose ether, such as carboxymethylcellulose. Carboxymethylcellulose is available from a variety of commercial sources, including but limited to, Sigma, Hercules, Fluka and Noviant. In certain embodiments, the average molecular weight of the cellulose ether is at least about 1000 daltons, such as at least about 5000 daltons, where the average molecular weight may be as high as 10,000 daltons or higher, e.g., 50,000 daltons or higher, 100,000 daltons or higher, and ranges in certain embodiments from about 5,000 to about 100,000 daltons, such as from about 10,000 to about 50,000 daltons.

The proportion of the emulsifying agent in the cement in certain embodiments ranges from about 0.01 to about 10% (w/w), such as from about 0.05 to about 2.0% (w/w).

When employed, the emulsifying agent may be included in one or both of the above liquid and dry reactant components.

In certain embodiments, the subject cement compositions may be seeded with any of a variety of cells, as described in published U.S. Patent Application No. 20020098245, now U.S. Pat. No. 6,719,993, the disclosure of which is herein incorporated by reference.

In addition, in certain embodiments the compositions include demineralized bone matrix, which may be obtained typically in a lyophilized or gel form and is combined with the cement composition at some prior to implantation. A variety of demineralized bone matrixes are known to those of skill in the art and any convenient/suitable matrix composition may be employed.

One or both of the above liquid and dry reactant components may include one or more additional agents, as desired, such as an imaging or contrast agent (e.g., barium containing agents), or an active agent that modulates the properties of the product into which the composition prepared by the subject method sets. Such additional ingredients or agents include, but are not limited to: organic polymers, e.g., proteins, including bone associated proteins which impart a number of properties, such as enhancing resorption, angiogenesis, cell entry and proliferation, mineralization, bone formation, growth of osteoclasts and/or osteoblasts, and the like, where specific proteins of interest include, but are not limited to: osteonectin, bone sialoproteins (Bsp), α-2HS-glycoproteins, bone Gla-protein (Bgp), matrix Gla-protein, bone phosphoglycoprotein, bone phosphoprotein, bone proteoglycan, protolipids, bone morphogenic protein, cartilage induction factor, platelet derived growth factor, skeletal growth factor, and the like; particulate extenders; inorganic water soluble salts, e.g., NaCl, calcium sulfate; sugars, e.g., sucrose, fructose and glucose; pharmaceutically active agents, e.g., antibiotics; and the like In practicing the subject methods, suitable amounts of the dry reactants (which includes the monovalent cation dihydrogen phosphate salt) and the setting fluid are combined to produce a settable composition. In other words, the ratio of the dry reactants to setting fluid (i.e. the liquid to solids ratio)

is selected to provide for a "settable" composition, where by "settable" composition is meant a composition that goes from a first non-solid (and also non-gaseous) state to a second, solid state after setting. In many embodiments, the liquid to solids ratio is chosen to provide for a flowable composition that goes from a first, non-solid state to a second, solid state, where in many embodiments the flowable composition has a viscosity ranging from that of milk to that of modeling clay. As such, the liquids to solids ratio employed in the subject methods typically ranges from about 0.2 to 1.0, usually from about 0.3 to 0.6. Of particular interest in many embodiments are methods that produce a paste composition, where the liquid to solids ratio employed in such methods typically ranges form about 0.25 to 0.5, usually from about 0.3 to 0.45.

As mentioned above, the requisite amounts of dry reactants, setting fluid and contrast agent (which may be separate from or present in one or both of the dry reactants and setting fluid) are combined under conditions sufficient to produce the product composition. As such, the dry and liquid components are typically combined under agitation or mixing conditions, such that a homogenous composition is produced from the dry and liquid components. Mixing may be accomplished using any convenient means, including manual mixing as described in U.S. Pat. No. 6,005,162 and automated mixing as described in WO 98/28068, the disclosures of which are herein incorporated by reference. Also of interest is the device disclosed in U.S. Pat. No. 5,980,482, the disclosure of which is herein incorporated by reference.

In certain embodiments, a simple cylindrical tube may be used both as a storage and packaging device and a mixing and delivery device. The plastic tube or analogous containment structure is separated into at least two sections, compartments or portions. One section or portion contains the powder component, as described above. The at least one more compartment contains the setting fluid, where in certain embodiments, two or more compartments for setting fluid components are provided, e.g., where it is desired to keep the disparate components of the setting fluid separate prior to use, and/or where one desires to have flexibility in determining the amounts of the phosphate and silicate ions in the setting fluid that is employed. For example, one may have a two-compartment device with powder in one component and a setting fluid in the other. In other embodiments, one may have a three compartment device, with powder in a first compartment, silicate solution in a second compartment and phosphate solution in a third compartment. In yet other embodiments, one may have a multi-compartment device, with powder in a first compartment, a solution at one concentration of either or both component ions in a second compartment, and a solution at a second concentration of either or both component ions in a third compartment, etc., where this type of embodiment allows one to "tailor" the setting fluid employed depending on the particular application in which the cement is to be used. In yet other embodiments, one may have a three-compartment device with powder in the middle component and setting solution in the two outer components, where each setting solution may be the same or different. Additional compartments may be present for additional components as desired, e.g., water-soluble contrast agent, cement modifiers, etc.

The two or more compartments are separated from each other by an easily removable barrier that can be readily removed during preparation of the packaged cement. Any convenient removable barrier may be present in the device, where a representative barrier means of interest is a dialysis bag clip or analogous means. Another representative barrier means of interest is a frangible barrier, as described in WO 98/28068 and U.S. Pat. No. 5,362,654; the disclosures of which are herein incorporated by reference. When one is ready to mix, the clip or other barrier means between the areas (liquid(s) and powder) is removed (e.g., unclipped), and the contents are simply kneaded together by hand or other technique. The above steps may be performed through a second outer covering for sterility—i.e., the above-described package elements may be present in a second outer covering for sterility. The outer covering may then be removed and the mixed contents from the tube may be delivered from one end of the storage/mixing tube using a peristaltic action.

The above-described packaging may be further modified to include one or more additional components that are employed during use/delivery of the product composition, such as removable delivery elements, elements for transferring the product cement into an attached delivery element, elements that assist in combining the components to produce the desired product composition, etc.

Representative mixing devices and methodologies are further described in: U.S. Pat. No. 6,375,935; as well as pending application Ser. No. 10/462,075; 10/629,321, now U.S. Pat. No. 7,306,786; Ser. Nos. 10/717,171; 10/661,356, now U.S. Pat. No. 7,261,717; and Ser. No. 10/109,994, now U.S. Pat. No. 6,719,993; the disclosures of which are herein incorporated by reference.

The temperature of the environment in which combination or mixing of the dry and liquid components takes place is sufficient to provide for a product that has desired setting and strength characteristics, and typically ranges from about 0 to 50° C., usually from about 20 to 30° C. Mixing takes place for a period of time sufficient for the composition to be produced, and generally takes place for a period of time ranging from about 15 to 120 seconds, usually from about 15 to 100 seconds and more usually from about 15 to 60 seconds.

In certain embodiments of the subject invention, vibration is used in conjunction with at least the preparation of the orthopedic cement. By used in conjunction with the preparation of an orthopedic cement is meant that vibration is employed at some point during the period in which the cement precursors of the cement, e.g., liquid and solid reagents or cement components, are combined to produce a flowable cement product composition. With many orthopedic cements of interest, dry and liquid precursors, e.g., a powder and setting liquid, are combined to a produce a flowable cement composition product that, over time, sets into a solid material. In certain embodiments of the subject invention, vibration is employed by applying a vibratory force, e.g., sonic or mechanical, to the precursors of the flowable composition, e.g., during mixing of the precursors. For example, in certain representative embodiments, vibration may be applied to the container or vessel, e.g., syringe, in which the flowable cement composition is prepared, and thereby applied to the flowable cement composition as it is being prepared.

In certain of these representative embodiments, the vibratory force that is applied to the cement may have a frequency ranging from about 0.1 Hz to about 100,000 Hz, such as from about 5 Hz to about 50,000 Hz, including from about 100 Hz to about 5000 Hz, and an amplitude ranging from about 1 angstrom to about 5 mm, such as from about 1 micron to about 1 mm, including from about 10 micron to about 500 micron.

The vibratory force may be applied to the cement components for the duration of the preparatory time or for a portion thereof, e.g., while the initial components are combined, while additives are combined with the product of mixing of the initial components, etc. In certain representative embodiments, vibration is applied for a duration ranging from about 1 sec to about 5 minutes, such as from about 10 sec to about 1 minute, including from about 15 sec to about 30 sec. Such embodiments are further described in application Ser. Nos. 10/661,356 and 10/797,907, now U.S. Pat. No. 7,252,672; the disclosures of which are herein incorporated by reference.

The above-described protocols result in a settable composition that is capable of rapidly setting into a calcium phosphate mineral product having high strength, as described in greater detail below.

Settable Compositions

The settable compositions produced by the above-described methods are compositions that rapidly set into a biologically compatible, and often resorbable and/or remodelable, high-strength product, where the product is characterized by including calcium phosphate molecules not present in the initial reactants, i.e., that are the product of a chemical reaction among the initial reactants.

In representative embodiments, the settable compositions are flowable. The term "flowable" is meant to include paste-like compositions, as well as more liquid compositions. As such, the viscosity time of the subject flowable compositions, defined as time periods under which the mixed composition injects through a standard Luer-lok fitting after mixing, typically ranges up to about 10 minutes, usually up to about 7 minutes, such as up to about 4 minutes. Of particular interest in many embodiments are paste compositions that have an injectable viscosity that injects in a time period ranging up to about 5 minutes, such as about up to about 4 minutes. Pastes that stay paste-like for longer period may be displaced by bleeding bone once implanted into the body, which create a blood interface between the cement and the bone prior to the cement hardening.

The compositions produced by the subject invention set into calcium phosphate mineral containing products. By "calcium phosphate mineral containing" product is meant a solid product that includes one or more, usually primarily one, calcium phosphate mineral. In many embodiments, the calcium phosphate mineral is one that is generally poorly crystalline, so as to be resorbable and, often, remodelable, over time when implanted into a physiologically site. The calcium to phosphate ratio in the product may vary depending on particular reactants and amounts thereof employed to produce it, but typically ranges from about 2:1 to 1.33:1, usually from about 1.8:1 to 1.5:1 and more usually from about 1:7:1 to 1.6:1. Of particular interest in many embodiments are apatitic products, which apatitic products have a calcium to phosphate ratio ranging from about 2.0:1 to 1.33:1, including both hydroxyapatite and calcium deficient analogs thereof, including carbonate substituted hydroxyapatite (i.e. dahllite), etc. The subject composition is, in many embodiments, one that is capable of setting into a hydroxyapatitic product, such as a carbonated hydroxyapatite, i.e. dahllite, having a carbonate substitution of from about 2 to about 10%, usually from about 2 to about 8% by weight of the final product.

The period of time required for the compositions to harden or "set" may vary. Setting is determined by the Gilmore Needle Test (ASTM C266-89), modified with the cement submerged under 37° C. physiological saline, where setting is defined as the time period following preparation when the compositions resists indentation by a needle applied at a force of 135 Newtons. The set times of the subject cements may range from about 30 seconds to 20 minutes, and will in certain embodiments range from about 30 seconds to about 10 minutes. In many embodiments, the flowable composition sets in a clinically relevant period of time. By clinically relevant period of time is meant that the paste-like composition sets in less than about 30 minutes, usually less than about 25 minutes, where the composition remains flowable for at least about 3 minutes, sometimes at least about 5 minutes following combination or mixture of the precursor liquid and dry cement components.

A feature of the rapidly setting compositions is that they rapidly set into a high strength product, as determined by the Gilmore Needle Test (ASTM C266-89) in terms of setting value. More specifically, the compositions attain high strength rapidly, such that they may be viewed as rapid strength attainment compositions. As such, at 3 minutes the compositions have a setting value of at least about 50 Newtons, such as at least about 75 Newtons, where the setting value may be as high as 100, 150, 175 or more, e.g., 250 or more, Newtons. At 6 minutes the compositions have a setting value of at least about 250 Newtons, such as at least about 275 Newtons, where the setting value may be as high as 400, 450, 475 or more (e.g., 500 or more) Newtons. At 9 minutes the compositions have a setting value of at least about 425 Newtons, such as at least about 450 Newtons, where the setting value may be as high as 600, 700, 725 or more Newtons. At 12 minutes the compositions have a setting value of at least about 600 Newtons, such as at least about 650 Newtons, where the setting value may be as high as 700, 750, 775 or more, e.g., 1200 or more, Newtons.

A feature of the subject compositions is that they are manipulatable while they are setting into a solid product. As such, they may be manipulated during the setting process without adversely affecting the properties of the final product. For example, during the setting process, screws can be drilled into them, without adversely impacting the properties of the final product.

In certain embodiments, the settable compositions are characterized as compositions that go through the following phases: (1) a working phase in which the composition may be manipulated, e.g., delivered to a bone defect site; (2) a setting phase, in which the composition should be maintained without manipulation; (3) a "drillable" phase, in which hardware, such as screws, may be inserted or positioned into the composition; and (4) a screw tightening phase, in which screws positioned in the composition during the "drillable" phase may be tightened without adversely affecting the composition. In certain embodiments, the working phase ranges from about 0.5 minutes to about 5.0 minutes, e.g., from about 0.5 minutes to about 4.0 minutes following mixing of the components. In certain embodiments, the setting phase ranges from about 1 minute to about 15 minutes, e.g. from about 1 minutes to about 10 minutes following mixing of the components. In certain embodiments the drillable phase commences from about 5 minutes to about 10 minutes following mixing of the components, and may extend to about 10 minutes to about 15 minutes or longer following mixing of the components. In certain embodiments, the screw tightening phase ranges comments from about 10 minutes to about 15 minutes following mixing of the components.

In one representative embodiment, the working phase ranges from about 0 to about 2 minutes, e.g., from about 0.5 to about 1 minute following mixing of the components. In this embodiment, the setting phase occurs during the period from about 1 minute to about 5 minutes following mixing of the components. In this embodiment, the drillable phase occurs during the period from about 5 minute to about 10 minutes following mixing of the components. In this embodiment, the screw-tightening phase commences at about 10 minutes following mixing of the components.

In another representative embodiment, the working phase lasts up to about 5 minutes, and usually up to about 4 minutes, including 3 minutes, following mixing of the components. In this embodiment, the setting phase occurs during the period from about 4 minutes to about 10 minutes following mixing of the components. In this embodiment, the drillable phase occurs during the period from about 10 minutes to about 15 minutes following mixing of the components. In this embodiment, the screw-tightening phase commences at about 15 minutes following mixing of the components.

The compressive strength of the product into which the flowable composition sets may vary significantly depending on the particular components employed to produce it. Of particular interest in many embodiments is a product that has a compressive strength sufficient for it to serve as at least a cancellous bone structural material. By cancellous bone structural material is meant a material that can be used as a cancellous bone substitute material as it is capable of withstanding the physiological compressive loads experienced by compressive bone under at least normal physiological conditions. As such, the subject flowable paste-like material is one that sets into a product having a compressive strength of at least about 20, usually at least about 40 and more usually at least about 50 MPa, as measured by the assay described in Morgan, E F et al., 1997, Mechanical Properties of Carbonated Apatite Bone Mineral Substitute: Strength, Fracture and Fatigue Behavior. J. Materials Science: Materials in Medicine. V. 8, pp 559-570, where the compressive strength of the final apatitic product may be as high as 60 MPa or higher. Inclusion of the silicate in the setting liquid allows lower liquid to solids ratios to be employed which results in significantly higher compressive strengths. Compressive strengths can be obtained that range as high 100 to 200 MPa. In certain embodiments, the resultant product has a tensile strength of at least about 0.5 MPa, such as at least about 1 MPa, including at least about 5 MPa, at least about 10 MPa or more, e.g., from about 0.5 to about 10 MPa, as determined by the tensile strength assay appearing in the Experimental Section, below.

In representative embodiments, the resultant product is stable in vivo for extended periods of time, by which is meant that it does not dissolve or degrade (exclusive of the remodeling activity of osteoclasts) under in vivo conditions, e.g., when implanted into a living being, for extended periods of time. In these embodiments, the resultant product may be stable for at least about 4 months, at least about 6 months, at least about 1 year or longer, e.g., 2.5 years, 5 years, etc. In certain embodiments, the resultant product is stable in vitro when placed in an aqueous environment for extended periods of time, by which is meant that it does not dissolve or degrade in an aqueous environment, e.g., when immersed in water, for extended periods of time. In these embodiments, the resultant product may be stable for at least about 4 months, at least about 6 months, at least about 1 year or longer, e.g., 2.5 years, 5 years, etc.

In representative embodiments, the composition is capable of setting in a fluid environment, such as an in vivo environment at a bone repair site. As such, the composition can set in a wet environment, e.g., one that is filled with blood and other physiological fluids. Therefore, the site to which the composition is administered during use need not be maintained in a dry state.

Applications

The subject methods and compositions produced thereby, as described above, find use in applications where it is desired to introduce a material capable of setting up into a solid calcium phosphate product into a physiological site of interest, such as in dental, craniomaxillofacial and orthopedic applications. In orthopedic applications, the cement will generally be prepared, as described above, and introduced to a bone repair site, such as a bone site comprising cancellous and/or cortical bone. Orthopedic applications in which the cements prepared by the subject system find particular use include the treatment of fractures and/or implant augmentation, in mammalian hosts, particularly humans. In such fracture treatment methodologies, the fracture is first reduced. Following fracture reduction, a flowable structural material prepared by the subject system is introduced into the cancellous tissue in the fracture region using the delivery device described above. Specific dental, craniomaxillofacial and orthopedic indications in which the subject invention finds use include, but are not limited to, those described in U.S. Pat. No. 6,149,655, the disclosure of which is herein incorporated by reference. In addition to these particular applications described in this U.S. patent, the subject cement compositions also find use in applications where a sternotomy has been performed. Specifically, the subject cements find use in the closure process of a sternotomy, where the bone fragments are rejoined and wired together, and any remaining cracks are filled with the subject cement. In yet other embodiments, the subject compositions find use in drug delivery, where they are capable of acting as long lasting drug depots following administration to a physiological site. See e.g. U.S. Pat. Nos. 5,904,718 and 5,968,253; the disclosures of which are herein incorporated by reference.

In certain embodiments, vibration is employed in conjunction with at least preparation of the target bone site. In the subject methods, the target bone site may be any of a variety of different bone sites. In many embodiments, the target bone site is an interior target bone site, e.g., an interior region of a bone, as a cancellous domain bounded by cortical walls. Often, the target bone site is made up of cancellous tissue, into which it is desired to penetrate the orthopedic cement to produce a cancellous bone/cement composite structure. Representative cancellous bone target sites of interest include, but are not limited to, those found in: vertebral bodies, Colles' fractures, proximal humerus fractures, tibial plateau fractures, calcaneous fractures, and the like.

In these embodiments, vibration may be applied to the target bone site using any convenient protocol, depending on the desired outcome of the use vibration in target bone site preparation. For example, in certain embodiments, preparation of the target bone site may include removal of marrow an other materials from the bone site, e.g., the methods may include a marrow or hematoma removal step, where material, e.g., marrow, hematoma, at the target site is removed, e.g., before and/or during delivery of the cement composition, so as to further enhance penetration of the cement into the target site. For example, the marrow may be removed by aspiration from the target bone site. More specifically, marrow may be aspirated from one side of the target site before or as cement is introduced into the other side. In these embodiments, a vibratory force may be applied to the target bone site to enhance the rate and/or efficiency of marrow, e.g., fatty marrow, removal.

In certain of these representative embodiments, the vibratory force that is applied to the target bone site may have a frequency ranging from about 1 Hz to about 100,000 Hz, such as from about 10 Hz to about 10,000 Hz, including from about 100 Hz to about 1000 Hz, and an amplitude ranging from about 1 Angstrom to about 5 mm, such as from about 1 micron to about 100 micron, including from about 5 micron to about 50 micron. In certain representative embodiments, vibration is applied for a duration ranging from about 0.1 sec to about 10 minutes, such as from about 1 sec to about 5 minute, including from about 10 second to about 1 minute.

In certain embodiments, vibration is employed in conjunction with delivery of the cement to a target site. In other words, a vibratory force is applied to the cement composition during delivery to the target site, such as a target bone site. Put another way, the cement composition is vibrated as it is being delivered to the target bone site.

While the cement composition may be vibrated using any convenient protocol, in many embodiments the cement is vibrated by applying vibratory force to a cement delivery element, e.g., needle, which is conveying the cement to the target bone site. The amount of vibratory force that is applied to the cement, e.g., through application to the delivery element, is typically sufficient to provide for highly controlled penetration of the cement through cancellous bone tissue. By "highly controlled penetration" is meant penetration of the cement through cancellous bone tissue in manner that can be stopped at substantially the same time as cessation of vibration, such that when vibration stops, the cement no longer moves further into the cancellous tissue, and any movement of the cement into the cancellous tissues continues for no more than about 5 seconds, such as no more than about 1 to about 3 seconds. Where the vibratory force is applied to the cement by applying it to a delivery element for the cement, the delivery element is, in many embodiments, vibrated in the range of about 1 to 100,000 Hz, such as from about 10 to 10,000 vpm, including from about 100 to about 1,000 Hz, and with a force that moves the delivery element a distance in magnitude in either direction of from about 1 Angstrom to about 5.0 mm, such as from about 1 micron to about 100 micron, such as from 5 micron to 50 micron.

A feature of the subject methods of certain of these embodiments is that the cement is delivered in manner that provides for highly controlled penetration without the use of significant back-pressure on the cement. As such, any pressure applied to the cement during delivery does not exceed about 100 psi, and is between about 1 and 100 psi in certain embodiments. In certain of these embodiments, a negative pressure may be present at the target delivery site, which negative pressure enhances entry of the cement composition to the target site. The negative pressure may be produced using any convenient protocol, e.g., the target site preparation protocol described above. Where a negative pressure is present at the target delivery site, the negative pressure may range from about 1 to about 1000 psi, including from about 10 to about 100 psi.

Use of vibration in the preparation of a delivery site and/or delivery of a cement to a site is further described in application Ser. Nos. 10/661,356 and 10/797,907; the disclosures of which are herein incorporated by reference.

Kits

Also provided are kits comprising the subject cements, where the dry and liquid components may be present in separate containers in the kit, or some of the components may be combined into one container, such as a kit wherein the dry components are present in a first container and the liquid components are present in a second container, where the containers may or may not be present in a combined configuration, as described in U.S. Pat. No. 6,149,655, the disclosure of which is herein incorporated by reference. In certain embodiments, the kits may include two or more setting fluids in different concentrations, e.g., where one wishes to provide a kit with flexibility with respect to the nature of the setting fluid that is prepared therefrom. For example, a kit may include two more different phosphate-silicate solutions that differ from each other with respect to their silicate and/or phosphate components. Alternatively, the kit may include two or more different, separate phosphate and/or silicate solutions that differ from each other in terms of concentration and that are mixed upon use of the kit as desired to obtain a desired setting fluid. As mentioned above, the kit components may be present in separate containers. Alternatively, the components may be present as a packaged element, such as those described above.

In addition to the cement compositions, the subject kits may further include a number of additional reagents, e.g., cells (as described above, where the composition is to be seeded), protein reagents (as described above), and the like.

The subject kits may further include one or more additional components that find use in the preparation and/or delivery of the cement, e.g., mixing elements, such as spatulas, mortars, pestles, etc.; delivery elements, e.g., syringes, etc.; and the like.

In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following examples are offered by way of illustration and not by way of limitation.

EXPERIMENTAL

1. Rapid Setting Cement Formulations

A. Introduction

Cement formulas were investigated consisting of a mixture of α-tricalcium phosphate and dicalcium phosphate anhydrous mixed with dilute sodium silicate pH=11.0 using a liquid to powder ration of 0.40. The specific formulas tested were:

B. Cement Formulas:

6.0 g TCP 3082102
0.6 g DCPA
0.17 g MCPM or SPMA
2.71 g NaSiO4 (2.5 vol. %, 0.40 l/s, pH 11.0)
6.0 g TCP 3082102
0.6 g DCPA
0.19 g SPMM
2.71 g NaSiO4 (2.5 vol. %, 0.40 l/s, pH 11.0)

C. Results

The effects of different dihydrogen phosphate salts added in powder form and mixed within the same cement system were evaluated in terms of early strength attainment (setting) as measured by a modified Gilmore needle indentation test.

The salts tested included the following:

| Name | Source | Molecular Form. | MW | Weight per Mole of (H2PO4-) |
|---|---|---|---|---|
| MCPM | JTBaker | Ca(H2PO4)2•H2O | 252.1 | 126.0 |
| SPMA | Sigma | NaH2PO4 | 120.0 | 120.0 |

-continued

| Name | Source | Molecular Form. | MW | Weight per Mole of (H2PO4-) |
|---|---|---|---|---|
| SPMM | Sigma | NaH2PO4•H2O | 138.0 | 138.0 |

Note:
Moles of Phosphate will be nearly equal with substitution of MCPM by SPMA.

Both monobasic sodium phosphate anhydrous (SPMA) and monobasic sodium phosphate monohydrate (SPMM) salts were superior to monobasic calcium phosphate monohydrate (MCPM) as demonstrated by the following setting test results.

| | Setting Values (Newtons) | | |
|---|---|---|---|
| | MCPM | SPMA | SPMM |
| 3 min | 2.3 | 82.0 | 183 |
| 6 min | 4.8 | 299.0 | 509 |
| 9 min | 131.8 | 469.0 | 725 |
| 12 min | 190.6 | 664.3 | 800 |

II. Rapid Setting Cement Formulations with Carboxymethylcellulose

A. Introduction

The effect of the addition of carboxymethylcellulose to the commercially available Callos Inject cement formulation (Skeletal Kinetics LLC, Cupertino Calif.) was observed.

B. Formulations

1. Inject Formulation w/CMC:
   1 g 40-100 micron alpha TCP
   1 g 100-200 micron alpha TCP
   5 g 3-4 micron alpha TCP
   0.1 g sodium phosphate
   0.015 g CMC
   1:100 dilution sodium silicate at 0.41 l/s
2. Impact Formulation w/CMC:
   3 g 100-200 micron alpha TCP
   8 g 3-4 micron alpha TCP
   0.125 g sodium phosphate
   0.03 g CMC
   1:50 dilution sodium silicate at 0.39 l/s

C. Results

1. Injection Testing (N=6)

Injection testing was performed through Merit Medallion 6 cc Syringes with designated Mannin 11 gauge needle. The material was mixed according to Instructions for Use (IFU): adjust room temperature to 19-21° C., mix powder and liquid for 1 minute, fill syringe, attach needle, inject under Instron machine at 3 minutes post-mix. The results are provided in Table 1, below. In Table 1 below, "Kit #" refers to the sample number of the powder-liquid set being used. "Start Volume (cc)" is the total amount of cement in the syringe measured from base of the luer to the volume mark on the syringe. "End Volume (cc)" is the amount of cement leftover in the syringe after the injection process is complete. "Dynamic Load (N)" is the median value of the load applied to the syringe plunger during the injection of the material. This value indicates the relative viscosity and ease of injection of the cement.

TABLE 1

| | Injection Test | | |
|---|---|---|---|
| Kit # | Start Volume (cc) | End Volume (cc) | Dynamic Load (N) |
| 1 | 3.5 | 0.0 | 15 |
| 2 | 3.5 | 0.0 | 10 |
| 3 | 3.5 | 0.0 | 11 |
| 4 | 3.5 | 0.0 | 12 |
| 5 | 3.5 | 0.0 | 11 |
| 6 | 3.5 | 0.0 | 11 |
| Average | 3.5 | 0.0 | 12 |
| Std.Dev. | 0.0 | 0.0 | 2 |

2. Intrusion Testing (N=6)

Intrusion testing was performed through multiple syringe diameters to assess intrusion capabilities. The material was mixed according to Instructions for Use (IFU): adjust room temperature to 19-21° C., mix powder and liquid for 1 minute, fill syringe, attach needle, inject under Instron machine at 3 minutes post-mix. The results are provided in Table 2, below. In Table 2, "Needle" refers to the gauge size of the needle diameter and the length of the needle.

TABLE 2

| | Injection Test | | | |
|---|---|---|---|---|
| Kit # | Needle | Start Volume (cc) | End Volume (cc) | Dynamic Load (N) |
| 1 | No needle | 3.4 | 0.0 | 12 |
| 2 | 11 g, 12 cm | 3.4 | 0.0 | 12 |
| 3 | 12 g, 12 cm | 3.4 | 0.0 | 15 |
| 4 | 13 g, 18 cm | 3.4 | 0.0 | 30 |
| 5 | 15 g, 13 cm | 3.4 | 0.0 | 40 |
| 6 | 16 g, 2 cm | 3.4 | 0.0 | 20 |
| Average | | 3.4 | 0.0 | |
| Std.Dev. | | 0.0 | 0.0 | |

3. Setting Testing (N=6)

Setting testing was performed as follows. The material was mixed according to IFU: mix for 1 minute, fill setting molds correctly, submerge in 32° C. bath at 2.5 minutes post-mix, test for setting values at designated times in bath under Instron machine. The results are provided in Table 3, below. In Table 3, "3 min, 6 min, 12 min (N)" are the designated times the setting cubes need to be submerged for, before being tested with the Instron machine.

TABLE 3

| | Setting Test | | |
|---|---|---|---|
| Kit # | 3 min (N) | 6 min (N) | 12 min (N) |
| 1 | 24.6 | 857.0 | 1064.0 |
| 2 | 9.0 | 778.1 | 1080.4 |
| 3 | 32.7 | 750.3 | 1052.7 |
| 4 | 54.2 | 855.6 | 994.9 |
| 5 | 33.0 | 873.5 | 819.1 |
| 6 | 13.2 | 697.5 | 1108.9 |
| Average | 27.8 | 802.0 | 1020.0 |
| Std.Dev. | 16.3 | 71.0 | 105.4 |

4. Strength Testing (N=4)

Tensile strength testing was performed as follows. The material was mixed according to IFU: mix for 1 minute, fill tensile molds correctly, submerge in 37° C. bath for 24 hours, test for diametral tensile strength under Instron machine. The results are provide in Table 4, below.

TABLE 4

Tensile Test

| Kit # | | 24 hr | |
| --- | --- | --- | --- |
| 1 | 4.427 | 3.615 | 4.038 |
| 2 | 4.301 | 4.895 | 4.987 |
| 3 | 5.296 | 4.374 | 3.048 |
| 4 | 4.825 | 4.526 | 3.781 |
| Average | | 4.343 | |
| Std.Dev. | | 0.641 | |

5. Drill and Screw Test (N=6)

Drilling and screw testing was performed as follows. The material was mixed according to IFU: mix for 1 minute, fill drilling cube molds correctly, submerged in 32° C. bath for 10 minutes, drill hole in cement with ⅛" drill bit, and screw in self-drilling screw of matching diameter. The results are provided in Table 5. In Table 5, "Drilling" and "Screwing" are the observational descriptions for the functional outcome during the test.

TABLE 5

Drill and Screw Test

| Kit # | Drilling | Screwing |
| --- | --- | --- |
| 1 | No cracks/no problems | No cracks/no problems |
| 2 | No cracks/no problems | No cracks/no problems |
| 3 | No cracks/no problems | No cracks/no problems |
| 4 | No cracks/no problems | No cracks/no problems |
| 5 | No cracks/no problems | No cracks/no problems |
| 6 | No cracks/no problems | No cracks/no problems |
| Average | Good! | Good! |
| Std.Dev. | — | — |

6. Ease of Mixing

Ease of mixing was verified by mixing each of the above kits (kits used in testing section 1 to 5) following the Instructions for Use and noting the quality and consistency during and after mix. Mix quality was assured consistency by measure the weights of the Powder and Liquid, measuring pH levels of the Liquid, and calculating the Liquid:Solid ratio of the kits used in Setting and Injection tests.

The observational homogeneity of the mix was consistent throughout the testings. The kits mixed in a cream-like manner, though slightly thicker due to a higher viscosity formulation with CMC.

In Table 6 below, "Powder (g)" is the weight in grams of the powder component measured in one of the kits. "Liquid (g)" is the weight in grams of the liquid component measured in one of the kits. "pH" refers to the pH level of the liquid component. "L:S ratio" is the calculated ratio of liquid/solid weight.

TABLE 6

Ease of Mix/Consistency

| Kit # | Powder (g) | Liquid (g) | pH | L:S ratio |
| --- | --- | --- | --- | --- |
| 1 | 4.86 | 1.99 | 11.00 | 0.409 |
| 2 | 4.86 | 2.00 | 10.93 | 0.412 |
| 3 | 4.87 | 1.99 | 10.94 | 0.409 |
| 4 | 4.86 | 1.99 | 10.94 | 0.409 |
| 5 | 4.86 | 1.99 | 10.96 | 0.409 |
| 6 | 4.86 | 1.99 | 10.96 | 0.409 |
| 7 | 4.88 | 1.98 | 10.87 | 0.406 |
| 8 | 4.87 | 1.99 | 10.91 | 0.409 |
| 9 | 4.86 | 1.99 | 10.90 | 0.409 |

TABLE 6-continued

Ease of Mix/Consistency

| Kit # | Powder (g) | Liquid (g) | pH | L:S ratio |
| --- | --- | --- | --- | --- |
| 10 | 4.88 | 1.96 | 10.92 | 0.402 |
| 11 | 4.85 | 2.00 | 10.92 | 0.412 |
| 12 | 4.86 | 1.97 | 10.92 | 0.405 |
| Average | 4.86 | 1.99 | 10.93 | 0.408 |
| Std.Dev. | 0.01 | 0.01 | 0.03 | 0.003 |

7. Notch Sensitivity Test for Fracture Toughness

Notch Sensitivity testing was performed as follows. The material was mixed according to IFU: mix for 1 minute, fill notch sensitivity test molds correctly, submerge in 37° C. bath for the designated times. Two kits were used to completely fill one notch sensitivity mold. In order to assure maximum strength, the specimen was allowed to harden in a 37° C. bath for 4 days before testing. The results are provided in Table 7 below.

TABLE 7

Notch Sensitivity Test

| Kit # | 96 hr |
| --- | --- |
| 1 | 88N |

8. Summary

Table 8 the results for each test parameter reviewed above.

TABLE 8

| Test Feature | Result Summary |
| --- | --- |
| Injection | The cement injected 100% (end volume must be 0.0 cc leftover) |
| Intrusion | The cement was able to intrude through the modified injection device. |
| Setting | The cement reached ≥450N at 6 minutes curing in a 32° C. warm PBS bath. |
| Tensile Strength | The cement reached ≥4.0 MPa tensile strength after 24 hours of curing at 37° C. |
| Drill and Screw | The resultant hardened sample could be drilled and screwed after 10 min in a 32° C. PBS bath |
| Ease of Mix | The cement mixed with little effort within 1 min |

D. Conclusion

The above results demonstrate that the addition of carboxymethylcellulose to the inject formulation provides for complete injection of the cement, while other functions of the cement have remained similar to the original Callos™ Inject product. In addition, with respect to Impact formulations, show that the powders can mix well and do have better handling properties as compared to Impact formulations lacking carboxymethylcellulose.

It is evident from the above results and discussion that calcium phosphate cements that set rapidly into compositions with high strength are provided by the subject invention. As such, the subject invention represents a significant contribution to the art.

All publications and patent applications mentioned in this specification are herein incorporated by reference to the same extent as if each individual publication or patent application was specifically and individually indicated to be incorporated by reference.

The invention now being fully described, it will be apparent to one of skill in the art that many changes and modifications can be made thereto without departing from the spirit and scope of the appended claims.

What is claimed is:

1. A method of producing a calcium phosphate composition that sets into a calcium phosphate mineral containing product, said method comprising:
   combining:
   (a) a setting fluid;
   (b) dry reactants comprising:
      (i) calcium and phosphate sources comprising a first particulate calcium and/or phosphate reactant having a mean particle size of 8 µm or less and narrow particle size distribution; and a second calcium and/or phosphate reactant having a mean particle size that is 10 µm or greater; and
      (ii) a monovalent cation dihydrogen phosphate salt;
   in a ratio of (a) to (b) sufficient to produce said calcium phosphate mineral containing product that is resorbable over time when implanted into a physiological site, wherein the standard deviation of the particles that make up the first reactant does not exceed 4.0 um.

2. The method according to claim 1, wherein said monovalent cation dihydrogen phosphate salt includes at least one water of hydration.

3. The method according to claim 1, wherein said monovalent cation dihydrogen phosphate salt is described by the formula:

$$Y^+H_2PO_4 \cdot (H_2O)_n$$

where:
Y$^+$ is a monovalent cation; and
n is an integer from 0 to 2.

4. The method according to claim 3, wherein Y$^+$ is Na$^+$.

5. The method according to claim 1, wherein said monovalent cation dihydrogen phosphate salt is NaH$_2$PO$_4$ or NaH$_2$PO$_4 \cdot$H$_2$O.

6. The method according to claim 1, wherein said monovalent cation dihydrogen phosphate salt is present in said composition in an amount ranging from about 0.10 to about 10 wt %.

7. The method according to claim 1, wherein said method further comprises combining said dry reactants and setting fluid with an emulsifying agent.

8. The method according to claim 7, wherein said emulsifying agent is a cellulose ether.

9. The method according to claim 8, wherein said cellulose ether is carboxymethylcellulose.

10. The method according to claim 1, wherein said composition attains a strength of about 50 Newtons or greater in 3 minutes.

11. The method according to claim 1, wherein said composition attains a strength of about 250 Newtons or greater in 6 minutes.

12. A composition that sets into a calcium phosphate containing product, wherein said composition is produced by the method according to claim 1.

13. The composition according to claim 12, wherein said composition attains a strength of about 50 Newtons or greater in 3 minutes.

14. A method of repairing a hard tissue defect, said method comprising:
applying to the site of said defect a composition that sets into a calcium phosphate containing product, wherein said composition is produced by the method according to claim 1.

15. A kit for use in a preparing a composition that sets in an in vivo fluid environment into a calcium phosphate product, said kit comprising:
   (a) dry reactants comprising:
      (i) calcium and phosphate sources comprising a first particulate calcium and/or phosphate reactant having a mean particle size of 8 µm or less and narrow particle size distribution; and a second calcium and/or phosphate reactant having a mean particle size that is 10 µm or greater; and
      (ii) a monovalent cation dihydrogen phosphate salt; and
   (b) a setting fluid or components for producing the same.

16. The kit according to claim 15, wherein said kit further comprises an emulsifying agent.

17. The kit according to claim 16, wherein said emulsifying agent is a cellulose ether.

18. The kit according to claim 17, wherein said cellulose ether is carboxymethylcellulose.

19. The kit according to claim 15, wherein said kit further comprises a mixing element for preparing a settable composition from said dry reactants and setting fluid.

20. The kit according to claim 15, wherein said kit further comprises a delivery element.

21. A method of producing a calcium phosphate composition that sets into a calcium phosphate mineral containing product, said method comprising:
   combining:
   (a) a setting fluid;
   (b) dry reactants comprising:
      (i) calcium and phosphate sources comprising a first particulate calcium and/or phosphate reactant having a mean particle size of 8 µm or less and narrow particle size distribution; and a second calcium and/or phosphate reactant having a mean particle size that is 10 µm or greater; and
      (ii) a monovalent cation dihydrogen phosphate salt;
   in a ratio of (a) to (b) sufficient to produce said calcium phosphate mineral containing product that is resorbable over time when implanted into a physiological site,
   wherein samples of said composition attain an average setting strength of about 50 Newtons or greater in 3 minutes.

22. The method according to claim 21, wherein samples of said composition attain an average setting strength of about 75 Newtons or greater in 3 minutes.

23. The method according to claim 21, wherein samples of said composition attain an average setting strength of about 100 Newtons or greater in 3 minutes.

24. The method according to claim 21, wherein said composition attains a strength of about 150 Newtons or greater in 3 minutes.

25. The method according to claim 21, wherein said composition attains a strength of about 175 Newtons or greater in 3 minutes.

26. The method according to claim 21, wherein said composition attains a strength of about 250 Newtons or greater in 3 minutes.

27. The method according to claim 1, wherein the mean particle size of the second reactant is at least 2 times larger than the mean particle size of the first reactant.

* * * * *